United States Patent
Wright et al.

(10) Patent No.: US 11,850,757 B2
(45) Date of Patent: *Dec. 26, 2023

(54) DOCUMENTATION THROUGH A REMOTE PRESENCE ROBOT

(71) Applicant: InTouch Technologies, Inc., Goleta, CA (US)

(72) Inventors: Timothy C. Wright, Santa Barbara, CA (US); Fuji Lai, Goleta, CA (US); Marco Pinter, Goleta, CA (US); Yulun Wang, Goleta, CA (US)

(73) Assignee: TELADOC HEALTH, INC., Purchase, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/472,277

(22) Filed: Aug. 28, 2014

(65) Prior Publication Data

US 2015/0339452 A1 Nov. 26, 2015

Related U.S. Application Data

(63) Continuation of application No. 12/362,454, filed on Jan. 29, 2009, now Pat. No. 8,849,680.

(51) Int. Cl.
*B25J 9/16* (2006.01)
*H04N 7/18* (2006.01)
(Continued)

(52) U.S. Cl.
CPC ........ *B25J 9/1689* (2013.01); *G06Q 30/0283* (2013.01); *G16H 40/63* (2018.01);
(Continued)

(58) Field of Classification Search
CPC ....... B25J 9/1689; B25J 5/007; G06F 19/321; G06F 19/328; G06N 3/008; H04N 7/147;
(Continued)

(56) References Cited

U.S. PATENT DOCUMENTS

| | | |
|---|---|---|
| 4,107,689 A | 8/1978 | Jellinek |
| 4,213,182 A | 7/1980 | Eichelberger et al. |

(Continued)

FOREIGN PATENT DOCUMENTS

| | | |
|---|---|---|
| CN | 1404695 A | 3/2003 |
| CN | 1561923 A | 1/2005 |

(Continued)

OTHER PUBLICATIONS

Diggs, Alice C.; Design of a socially intelligent task selection software mechanism for a mobile robot; Tennessee State University. ProQuest Dissertations Publishing, 2008. 1456761. (Year: 2008).*

(Continued)

*Primary Examiner* — Hiep V Nguyen

(57) ABSTRACT

A robotic system that is used in a tele-presence session. For example, the system can be used by medical personnel to examine, diagnose and prescribe medical treatment in the session. The system includes a robot that has a camera and is controlled by a remote station. The system further includes a storage device that stores session content data regarding the session. The data may include a video/audio taping of the session by the robot. The session content data may also include time stamps that allow a user to determine the times that events occurred during the session. The session content data may be stored on a server that accessible by multiple users. Billing information may be automatically generated using the session content data.

20 Claims, 8 Drawing Sheets

(51) Int. Cl.
  *G06Q 30/0283* (2023.01)
  *G16H 40/67* (2018.01)
  *G16H 50/20* (2018.01)
  *G16H 40/63* (2018.01)
  *G16H 30/20* (2018.01)

(52) U.S. Cl.
  CPC ............ *G16H 40/67* (2018.01); *G16H 50/20* (2018.01); *H04N 7/185* (2013.01); *G05B 2219/45117* (2013.01); *G16H 30/20* (2018.01)

(58) Field of Classification Search
  CPC ............ H04N 7/00; H04N 7/18; H04N 7/185; H04N 7/181; G16H 40/40; G16H 40/67; G16H 50/20
  USPC .......................................................... 705/2
  See application file for complete search history.

(56) References Cited

U.S. PATENT DOCUMENTS

| | | | |
|---|---|---|---|
| 4,553,309 A | 11/1985 | Hess et al. | |
| 4,697,278 A | 9/1987 | Fleischer | |
| 5,220,263 A | 6/1993 | Onishi et al. | |
| 5,262,944 A | 11/1993 | Weisner et al. | |
| 5,400,068 A | 3/1995 | Ishida et al. | |
| 5,617,539 A | 4/1997 | Ludwig et al. | |
| 5,619,341 A | 4/1997 | Auyeung et al. | |
| 5,623,679 A | 4/1997 | Rivette et al. | |
| 5,734,805 A | 3/1998 | Isensee et al. | |
| 5,793,365 A | 8/1998 | Tang et al. | |
| 5,801,755 A | 9/1998 | Echerer | |
| 5,844,599 A | 12/1998 | Hildin | |
| 5,867,494 A | 2/1999 | Krishnaswamy et al. | |
| 5,872,922 A | 2/1999 | Hogan et al. | |
| 6,091,219 A | 7/2000 | Maruo et al. | |
| 6,189,034 B1 | 2/2001 | Riddle | |
| 6,195,683 B1* | 2/2001 | Palmer ................... H04N 7/147 348/E7.083 | |
| 6,292,713 B1 | 9/2001 | Jouppi et al. | |
| 6,292,714 B1 | 9/2001 | Okabayashi | |
| 6,304,050 B1 | 10/2001 | Skaar et al. | |
| 6,314,631 B1 | 11/2001 | Pryor | |
| 6,317,953 B1 | 11/2001 | Pryor | |
| 6,373,855 B1 | 4/2002 | Downing et al. | |
| 6,389,329 B1 | 5/2002 | Colens | |
| 6,411,055 B1 | 6/2002 | Fujita et al. | |
| 6,430,471 B1 | 8/2002 | Kintou et al. | |
| 6,507,773 B2 | 1/2003 | Parker et al. | |
| 6,529,620 B2 | 3/2003 | Thompson | |
| 6,535,793 B2 | 3/2003 | Allard | |
| 6,567,038 B1 | 5/2003 | Granot et al. | |
| 6,590,604 B1 | 7/2003 | Tucker et al. | |
| 6,597,392 B1 | 7/2003 | Jenkins et al. | |
| 6,667,592 B2 | 12/2003 | Jacobs et al. | |
| 6,674,259 B1 | 1/2004 | Norman et al. | |
| 6,693,585 B1 | 2/2004 | Macleod | |
| 6,724,823 B2 | 4/2004 | Rovati et al. | |
| 6,816,192 B1 | 11/2004 | Nishikawa | |
| 6,816,754 B2 | 11/2004 | Mukai et al. | |
| 6,893,267 B1 | 5/2005 | Yueh | |
| 6,951,535 B2* | 10/2005 | Ghodoussi .......... G06F 19/3418 600/101 | |
| 6,990,112 B1 | 1/2006 | Brent et al. | |
| 7,011,538 B2 | 3/2006 | Chang | |
| 7,053,578 B2 | 5/2006 | Diehl et al. | |
| 7,055,210 B2 | 6/2006 | Keppler et al. | |
| 7,219,364 B2 | 5/2007 | Bolle et al. | |
| 7,222,000 B2 | 5/2007 | Wang et al. | |
| 7,283,153 B2 | 10/2007 | Provost et al. | |
| 7,292,257 B2 | 11/2007 | Kang et al. | |
| 7,305,114 B2 | 12/2007 | Wolff et al. | |
| 7,332,890 B2 | 2/2008 | Cohen et al. | |
| 7,333,642 B2 | 2/2008 | Green | |
| 7,352,153 B2 | 4/2008 | Yan | |
| 7,363,121 B1 | 4/2008 | Chen et al. | |
| 7,467,211 B1 | 12/2008 | Herman et al. | |
| 7,483,867 B2 | 1/2009 | Ansari et al. | |
| 7,510,428 B2 | 3/2009 | Obata et al. | |
| 7,557,758 B2 | 7/2009 | Rofougaran | |
| 7,587,260 B2 | 9/2009 | Bruemmer et al. | |
| 7,631,833 B1 | 12/2009 | Ghaleb et al. | |
| 7,657,560 B1 | 2/2010 | DiRienzo | |
| 7,703,113 B2 | 4/2010 | Dawson | |
| 7,737,993 B2 | 6/2010 | Kaasila et al. | |
| 7,774,158 B2 | 8/2010 | Domingues Goncalves et al. | |
| 7,861,366 B2 | 1/2011 | Hahm et al. | |
| 7,885,822 B2 | 2/2011 | Akers et al. | |
| 7,956,894 B2 | 6/2011 | Akers et al. | |
| 7,957,837 B2 | 6/2011 | Ziegler et al. | |
| 7,982,769 B2 | 7/2011 | Jenkins et al. | |
| 8,126,960 B2 | 2/2012 | Obradovich et al. | |
| 8,212,533 B2 | 7/2012 | Ota | |
| 8,287,522 B2 | 10/2012 | Moses et al. | |
| 8,320,534 B2 | 11/2012 | Kim et al. | |
| 8,348,675 B2 | 1/2013 | Dohrmann | |
| 8,374,171 B2 | 2/2013 | Cho et al. | |
| 8,384,753 B1* | 2/2013 | Bedingfield, Sr. .... H04L 67/535 348/14.07 | |
| 8,400,491 B1 | 3/2013 | Panpaliya et al. | |
| 8,401,275 B2 | 3/2013 | Wang et al. | |
| 8,423,284 B2 | 4/2013 | O'Shea | |
| 8,451,731 B1 | 5/2013 | Lee et al. | |
| 8,515,577 B2 | 8/2013 | Wang et al. | |
| 8,610,786 B2 | 12/2013 | Ortiz | |
| 8,612,051 B2 | 12/2013 | Norman et al. | |
| 8,639,797 B1 | 1/2014 | Pan et al. | |
| 8,670,017 B2 | 3/2014 | Stuart et al. | |
| 8,726,454 B2 | 5/2014 | Gilbert et al. | |
| 8,836,751 B2 | 9/2014 | Ballantyne et al. | |
| 8,849,679 B2 | 9/2014 | Wang et al. | |
| 8,849,680 B2 | 9/2014 | Wright et al. | |
| 8,861,750 B2 | 10/2014 | Roe et al. | |
| 8,897,920 B2 | 11/2014 | Wang et al. | |
| 8,902,278 B2 | 12/2014 | Pinter et al. | |
| 2001/0051881 A1* | 12/2001 | Filler .................... G06F 19/322 705/3 | |
| 2002/0044201 A1 | 4/2002 | Alexander et al. | |
| 2002/0106998 A1 | 8/2002 | Presley et al. | |
| 2002/0109775 A1 | 8/2002 | White et al. | |
| 2002/0128985 A1 | 9/2002 | Greenwald | |
| 2002/0193908 A1* | 12/2002 | Parker .................... G06N 3/008 700/258 | |
| 2003/0080901 A1 | 5/2003 | Piotrowski | |
| 2003/0112823 A1 | 6/2003 | Collins et al. | |
| 2003/0120714 A1 | 6/2003 | Wolff et al. | |
| 2003/0135097 A1 | 7/2003 | Wiederhold et al. | |
| 2003/0195662 A1 | 10/2003 | Wang et al. | |
| 2003/0216833 A1 | 11/2003 | Mukai et al. | |
| 2004/0008138 A1 | 1/2004 | Hockley, Jr. et al. | |
| 2004/0017475 A1* | 1/2004 | Akers .................... G06Q 50/22 348/207.1 | |
| 2004/0019406 A1* | 1/2004 | Wang ...................... B25J 5/007 700/231 | |
| 2004/0088078 A1 | 5/2004 | Jouppi et al. | |
| 2004/0117067 A1 | 6/2004 | Jouppi | |
| 2004/0150725 A1 | 8/2004 | Taguchi | |
| 2004/0168148 A1 | 8/2004 | Goncalves et al. | |
| 2004/0218099 A1 | 11/2004 | Washington | |
| 2004/0260790 A1 | 12/2004 | Balloni et al. | |
| 2005/0052527 A1* | 3/2005 | Remy .................... H04N 7/181 348/14.08 | |
| 2005/0073575 A1 | 4/2005 | Thacher et al. | |
| 2005/0125083 A1 | 6/2005 | Kiko | |
| 2005/0149364 A1 | 7/2005 | Ombrellaro | |
| 2005/0152447 A1 | 7/2005 | Jouppi et al. | |
| 2005/0152565 A1 | 7/2005 | Jouppi et al. | |
| 2005/0168568 A1 | 8/2005 | Jouppi | |
| 2005/0264649 A1 | 12/2005 | Chang et al. | |
| 2005/0286759 A1 | 12/2005 | Zitnick et al. | |
| 2006/0010028 A1 | 1/2006 | Sorensen | |
| 2006/0056655 A1 | 3/2006 | Wen et al. | |
| 2006/0056837 A1 | 3/2006 | Vapaakoski | |
| 2006/0066609 A1 | 3/2006 | Iodice et al. | |

(56) References Cited

U.S. PATENT DOCUMENTS

| | | | |
|---|---|---|---|
| 2006/0071797 | A1 | 4/2006 | Rosenfeld et al. |
| 2006/0178559 | A1 | 8/2006 | Kumar et al. |
| 2007/0093279 | A1 | 4/2007 | Janik |
| 2007/0116152 | A1 | 5/2007 | Thesling |
| 2007/0170886 | A1 | 7/2007 | Plishner |
| 2007/0199108 | A1* | 8/2007 | Angle ............... B25J 5/007 318/568.12 |
| 2007/0226949 | A1 | 10/2007 | Hahm et al. |
| 2007/0290040 | A1 | 12/2007 | Wurman et al. |
| 2008/0027591 | A1 | 1/2008 | Lenser et al. |
| 2008/0033641 | A1 | 2/2008 | Medalia |
| 2008/0051985 | A1 | 2/2008 | D'Andrea et al. |
| 2008/0086241 | A1 | 4/2008 | Phillips et al. |
| 2008/0091340 | A1 | 4/2008 | Milstein et al. |
| 2008/0161969 | A1 | 7/2008 | Lee et al. |
| 2008/0232763 | A1 | 9/2008 | Brady |
| 2008/0263628 | A1 | 10/2008 | Norman et al. |
| 2008/0267069 | A1 | 10/2008 | Thielman et al. |
| 2009/0049640 | A1 | 2/2009 | Lee et al. |
| 2009/0055023 | A1* | 2/2009 | Walters ............... B25J 5/007 700/259 |
| 2009/0102919 | A1 | 4/2009 | Zamierowski et al. |
| 2010/0017046 | A1 | 1/2010 | Cheung et al. |
| 2010/0026239 | A1 | 2/2010 | Li et al. |
| 2010/0030578 | A1 | 2/2010 | Siddique et al. |
| 2010/0066804 | A1 | 3/2010 | Shoemake et al. |
| 2010/0171826 | A1 | 7/2010 | Hamilton et al. |
| 2010/0278086 | A1 | 11/2010 | Pochiraju et al. |
| 2010/0286905 | A1 | 11/2010 | Goncalves et al. |
| 2010/0301679 | A1 | 12/2010 | Murray et al. |
| 2011/0022705 | A1 | 1/2011 | Yellamraju et al. |
| 2011/0071675 | A1 | 3/2011 | Wells et al. |
| 2011/0072114 | A1 | 3/2011 | Hoffert et al. |
| 2011/0153198 | A1 | 6/2011 | Kokkas et al. |
| 2011/0193949 | A1 | 8/2011 | Nambakam et al. |
| 2011/0195701 | A1 | 8/2011 | Cook et al. |
| 2011/0280551 | A1 | 11/2011 | Sammon |
| 2011/0306400 | A1 | 12/2011 | Nguyen |
| 2012/0059946 | A1 | 3/2012 | Wang |
| 2012/0113856 | A1 | 5/2012 | Krishnaswamy |
| 2012/0203731 | A1 | 8/2012 | Nelson et al. |
| 2012/0291809 | A1 | 11/2012 | Kuhe et al. |
| 2013/0250938 | A1 | 9/2013 | Anandakumar et al. |
| 2014/0047022 | A1 | 2/2014 | Chan et al. |
| 2014/0085543 | A1 | 3/2014 | Hartley et al. |
| 2014/0135990 | A1 | 5/2014 | Stuart et al. |
| 2014/0139616 | A1 | 5/2014 | Pinter et al. |
| 2014/0155755 | A1 | 6/2014 | Pinter et al. |

FOREIGN PATENT DOCUMENTS

| | | | |
|---|---|---|---|
| CN | 1743144 A | 3/2006 | |
| CN | 101049017 A | 10/2007 | |
| CN | 101151614 A | 3/2008 | |
| CN | 100407729 C | 7/2008 | |
| JP | 11220706 A | 8/1999 | |
| JP | 2002321180 A | 11/2002 | |
| JP | 2004181229 A | 7/2004 | |
| JP | 2005111083 A | 4/2005 | |
| JP | 2009125133 A | 6/2009 | |
| WO | 9742761 A1 | 11/1997 | |
| WO | WO-2007041295 A2 * | 4/2007 | ............ B25J 11/008 |
| WO | 2009128997 A1 | 10/2009 | |

OTHER PUBLICATIONS

Fulbright et al., "SWAMI: An Autonomous Mobile Robot for Inspection of Nuclear Waste of Storage Facilities", Autonomous Robots, vol. 2, 1995, pp. 225-235.

Screenshot Showing Google Date for Lemaire Telehealth Manual, Screenshot Retrieved on Dec. 18, 2014, 1 page.

Nomadic Technologies, Inc., "Nomad Scout Language Reference Manual", Software Version: 2.7, Part No. DOC00002, Jul. 12, 1999, 47 pages.

"Appeal from the U.S. District Court for the Central District of California in No. 11-CV-9185, Judge Percy Anderson", May 9, 2014, pp. 1-48.

"Google translation of: Innovations Report", From research project to television star: Care-O-bot in ZDF series, http://www.innovations-report.de/specials/printa.php?id=5157, Sep. 28, 2001, 2 pages.

"MPEG File Format Summary", downloaded from: http://www.fileformat.info/format/mpeg/egff.htm, Feb. 1, 2001, 8 pages.

"Nomad Scout User's Manual", Nomadic Technologies, Software Version 2. 7, Part No. DOC00004, Jul. 12, 1999, pp. 1-59.

ACM Digital Library Record, "Autonomous Robots vol. 11 Issue 1", downloaded from <http://dl.acm.org/citation.cfm?id=591550&picked=prox&cfid=360891374&cftoken=35225929>, Jul. 2001, 2 pages.

Brenner, "A technical tutorial on the IEEE 802.11 protocol", BreezeCOM Wireless Communications, 1997, pp. 1-24.

CMU Course 16X62, "Robot user's manual", (describing the Nomad Scout), Carnegie Mellon University, Feb. 1, 2001, 11 pages.

Gostai, "Gostai Jazz: Robotic Telepresence", Available online at <http://www.gostai.com>, 4 pages.

Koenen, "MPEG-4: a Powerful Standard for Use in Web and Television Environments", (KPN Research), downloaded from http://www.w3.org/Architecture/1998/06/Workshop/paper26, Jul. 1, 1998, 4 pages.

Library of Congress, "008-Fixed-Length Data Elements (NR)", Mar. 21 Format for Classification Data, downloaded from http://www.loc.gov/marc/classification/cd008.html, Jan. 2000, pp. 1-14.

Osborn, "Quality of Life Technology Center", QoLT Research Overview:A National Science Foundation Engineering Research Center, Carnegie Mellon University of Pittsburgh, 2 pages.

Panusopone, et al., "Performance comparison of MPEG-4 and H.263+ for streaming video applications", Circuits Systems Signal Processing, vol. 20, No. 3, 2001, pp. 293-309.

Paulos, et al., "Personal Tele-Embodiment", Chapter 9 in Goldberg, et al., ed. "Beyond webcams", MIT Press, Jan. 4, 2002, pp. 155-167.

Paulos, "Personal tele-embodiment", OskiCat Catalog Record, UCB Library Catalog, 2001, 3 pages.

Paulos, "Personal Tele-Embodiment", Introductory and cover pages from 2001 Dissertation including Contents table, together with e-mails relating thereto from UC Berkeley Libraries, as shelved at UC Berkeley Engineering Library (Northern Regional library Facility), May 8, 2002, 25 pages, including 4 pages of e-mails.

Paulos, et al., "Social Tele-Embodiment: Understanding Presence", Autonomous Robots, vol. 11, Issue 1, Kluwer Academic Publishers, Jul. 2001, pp. 87-95.

Schraft, et al., "Care-O-bot™: the concept of a system fro assisting elderly or disabled persons in home enviornments", IEEE Proceedings of the 24th Annual Conference of the Industrial Electronics Society, IECON '98, Aug. 31-Sep. 4, 1998, pp. 2476-2481.

Mdeo Middleware Cookbook, "H.350 Directory Services for Multimedia", 2 pages.

* cited by examiner

FIG. 10

ADVANCED CONTROLS

| Start | Patient Info | NIHSS | t-PA | Summary |

272 — Patient Info
274 — NIHSS
276 — t-PA

270:
- Last Name: KANE
- First Name: JESSAMINE
- MRN: 3012296873
- Age: 75
- Gender: FEMALE
- Weight: 50.50 Kgs
- Patient History:
  - Diabetes ☐
- Heart Rate: 90

278

3:00:00
HR     90
BP     120/80
NHSS   3
View Images

FIG. 11

ADVANCED CONTROLS

| Start | Patient Info | NIHSS | t-PA | Summary |

274 — NIHSS

280:
MIH Stroke Scale:
- Level of Consciousness: Please Select: ▽
- MOC Questions:
  - Please Select:
  - 0 = Alert
  - 1 = Not alert
  - 2 = Not responsive
- LOC Commands:
- Best Gaze: Please Select: ▽

282

3:00:00
HR     84
BP     130/90
NHSS
View Images

FIG. 12

ADVANCED CONTROLS

| Start | Patient Info | NIHSS | t-PA | Summary |

276 — t-PA
294

290:
- Patient Weight: 77.7 Kgs
- Dosage Options: 292
  - 0.9 mg/kg ⦿
  - 0.6 mg/kg ○
- Calculate — 300
- Print Oder
- Total Dose: ____ Mg
- Bolus Dose: ____ Mg
  (administered iVP over 1 minute)
- 298
- Infusion Date: ____ Mg
  (to infuse over 60 minutes)

3:00:00 — 296
HR     84
BP     130/90
NHSS
View Images — 302

FIG. 13

DOCUMENTATION THROUGH A REMOTE PRESENCE ROBOT

BACKGROUND OF THE INVENTION

Cross-Reference to Related Applications

This application is a continuation of U.S. application Ser. No. 12/362,454, filed Jan. 29, 2009, now U.S. Pat. No. 8,849,680, the contents of which are hereby incorporated by reference in their entirety.

1. FIELD OF THE INVENTION

The subject matter disclosed generally relates to a robotic tele-presence system.

2. BACKGROUND INFORMATION

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

There has been marketed a mobile robot introduced by InTouch-Health, Inc., the assignee of this application, under the trademark RP-7. The InTouch robot is controlled by a user at a remote station. The remote station includes personal computer with a joystick that allows the user to remotely control the movement of the robot. Both the robot and remote station have cameras, monitors, speakers and microphones to allow for two-way video/audio communication.

The InTouch RP-7 system is used by medical personnel to remotely "visit" a patient. The system is particularly useful for medical specialist. For example, medical personnel specializing in patient stroke care can remotely examine, diagnose and prescribe a patient management plan. With the proliferation of such robots it would be desirable to track and store data related to tele-presence sessions.

BRIEF SUMMARY OF THE INVENTION

A robotic system with a robot that has a camera and a remote station coupled to the robot. The remote station controls the robot in a session that results in session content data. The system further includes a storage device that stores the session content data.

BRIEF DESCRIPTION OF THE DRAWINGS

FIG. 10 is a graphical user interface at the remote station;

FIG. 11 is a graphical user interface when a NIHSS tab is selected;

FIG. 12 is a graphical user interface displayed when a t-PA table is selected

FIG. 13 is a graphical user interface displayed when a view images button is selected.

DETAILED DESCRIPTION

Disclosed is a robotic system that is used in a tele-presence session. For example, the system can be used by medical personnel to examine, diagnose and prescribe medical treatment in the session. The system includes a robot that has a camera and is controlled by a remote station. The system further includes a storage device that stores session content data regarding the session. The data may include a video/audio taping of the session by the robot. The session content data may also include time stamps that allow a user to determine the times that events occurred during the session. The session data may be stored on a server that is accessible to multiple users. Billing information may be automatically generated using the session data.

Figure 1:
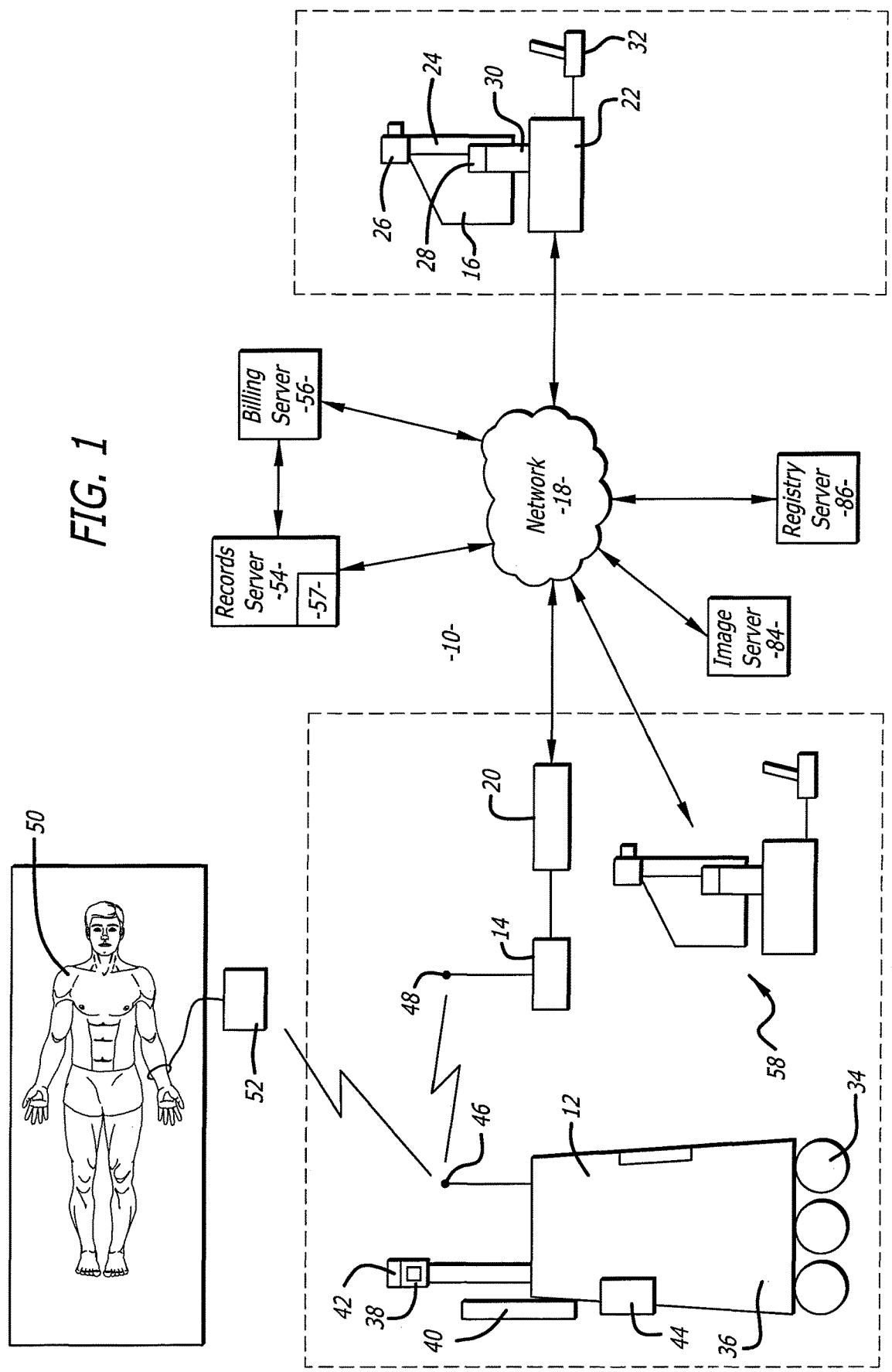
FIG. 1 is an illustration of a robotic system.

Referring to the drawings more particularly by reference numbers, FIG. 1 shows a robotic system 10. The robotic system 10 includes one or more robots 12. Each robot 12 may have a base station 14. The robot 12 is coupled to a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network 18 through, for example, a satellite.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. The robot 12 may also have a camera 38, a monitor 40, a microphone(s) 42 and a speaker(s) 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through operation of the input device 32. The robot camera 38 is coupled to the remote monitor 24 so that a user at the remote station 16 can view someone at the robot site such as a patient. Likewise, the robot monitor 40 is coupled to the remote camera 26 so that someone at the robot site can view the user. The microphones 28 and 42, and speakers 30 and 44, allow for audible communication between the robot site and the user of the system.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The system 10 can be used to engage in a session that results in data. For example, the system 10 can be used by medical personnel to remotely examine, diagnose and prescribe a patient management plan for a patient 50 in a medical session. Either the patient, or a bed supporting the patient, may have a radio frequency information device ("RFID") 52. The RFID 52 may wirelessly transmit information that is received by the robot 12 through antennae 46. The RFID information can be used to correlate a particular session with a specific patient. The receipt of RFID information may initiate the storage of session data. Although a medical session is described, it is to be understood that other types of sessions may be conducted with the system 10. For example, the system 10 may be used to move the robot(s) about a factory floor wherein the user provides remote consultation. Consultation session data may be stored by the system 10.

The system can store and display session content data. Session content data is information regarding the substance of a session. For example, in a medical application, session content data would include physician notes, diagnosis and prescription information. In a factory-equipment repair application, session content data would include repair methodology and replaced parts. Session content data would not be mere time entries associated with the logging on and termination of a robot session.

The system 10 may include a records server 54 and/or a billing server 56 that can be accessed through the network 18. The servers 54 and 56 may include memory, processors, I/O interfaces and storage devices such as hard disk drives, as is known in the art. Records server 54 may have a storage device(s) 57 that stores session data. The server 54 may receive and store session data during a session. For example, the server 54 may receive and store video and audio captured by the robot camera 38 and microphone 42, respectively. To reduce bandwidth requirements during a session the session data, such as video/audio segments, can be transmitted from the robot 12 to the server 54 after the session has terminated. For example, when the user logs off the system. Time-stamped progress notes are also simultaneously uploaded. The server 54 may contain other medical records of a patient such as written records of treatment, patient history, medication information, laboratory results, physician notes, etc. Video/audio segments can be timestamped and associated with the identification of the control station and the robot, and a unique identifier which can be cross-referenced with progress notes and other session data. These video/audio segments can then later be used to substantiate and reference the various progress notes and other events in a visual fashion. The system can track all head and base movements made during the course of the associated portion of the session, to allow correlation of those movements with the actions taken.

The system 10 may include a user interface 58 that allows a user at the remote location to enter data into the system. For example, the interface 58 may be a computer or a computer terminal that allows a user to enter information about the patient. The robot 12 can be moved into view of the patient through the remote station 16 so that patient information can be entered into the system while a physician is viewing the patient through the robot camera. The physician can remotely move the robot 12 to obtain different viewing angles of the patient. The user interface 58 may be a separate computer and/or be integral with the robot 12. The billing server 56 may automatically generate a bill from the information provided by the session data on a periodic basis. The billed elements may be based on either actions performed or outcomes achieved, or both. Alternatively, a user can manually generate bills through a user interface to the billing server.

The billing server 56 may receive session data during a session or upon termination of a session. Additionally, the billing server may poll a robot to retrieve data from its hard drive. The session data may be organized so as to automatically populate certain fields of a billing statement or report. The billing information can be automatically sent to an insurance carrier.

Figure 2:
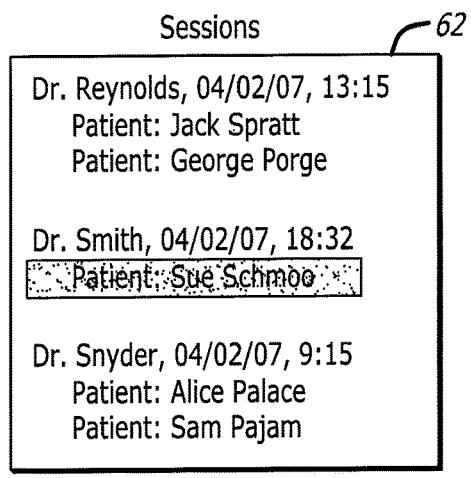
FIG. 2 is an illustration showing a user interface.
Figure 3:
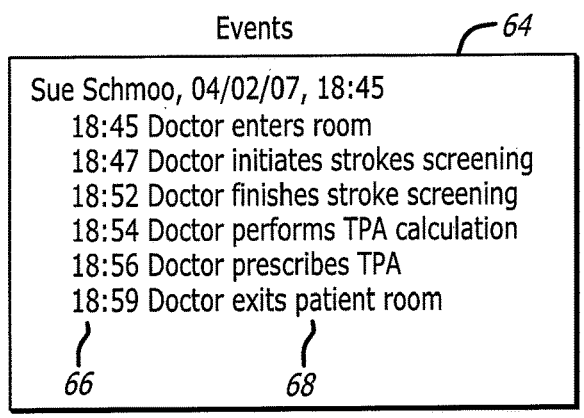
FIG. 3 is an illustration of a user interface displaying events and associated time stamps.

The server 54 can be accessible through a web page or other means for accessing information through a network 18. FIG. 2 shows a user interface 62 displayed at a remote station 16, or any other terminal that can access the server 54. The interface 62 can for example, provide a date and time that various physicians had sessions with different patients. FIG. 3 shows another user interface 64 that displays time stamps 66 that are associated with certain events 68. Records can be retrieved by various filters including physician name, patient name, time of session and services performed during the session. The event data can be initially stored in either the robot 12 or the remote station 16 and then loaded into the server 54, either during or after a session. Alternatively, event data can be directly loaded into the server without storing it locally on the robot or remote station.

Figure 4:
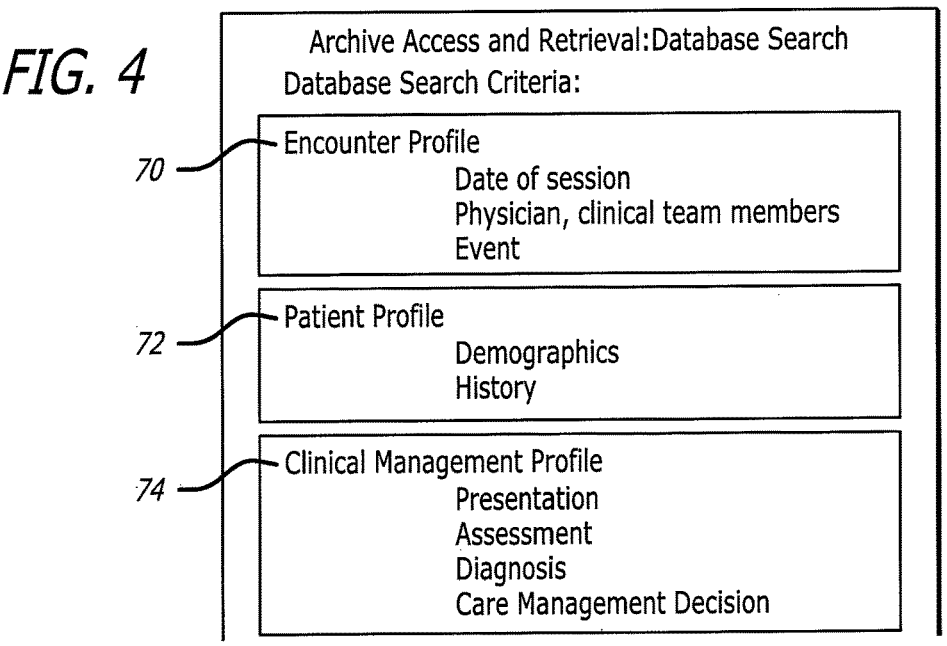
FIG. 4 is an illustration of a user interface with selectable fields.
Figure 5:
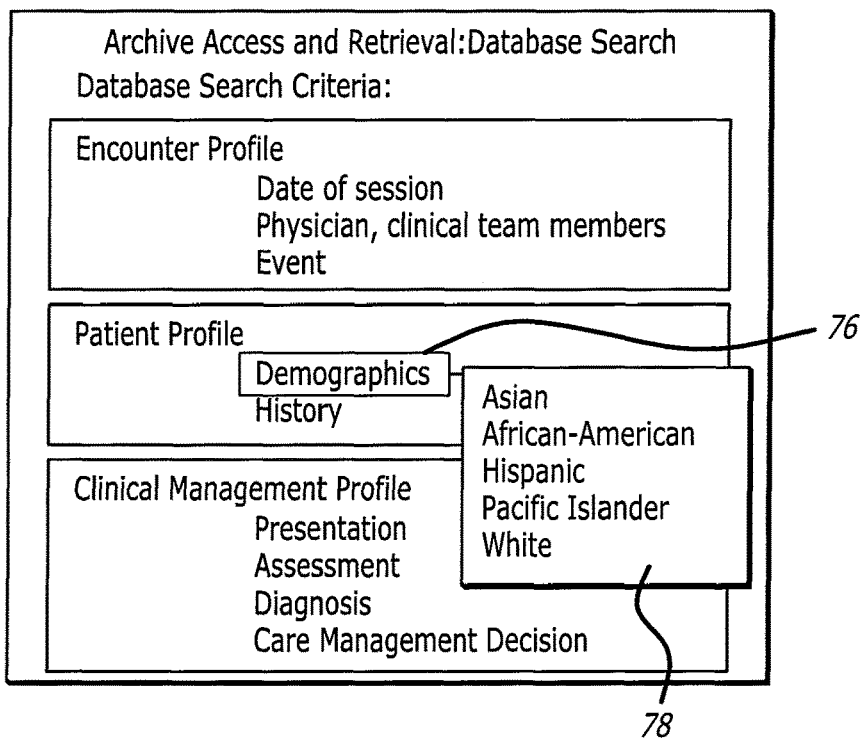
FIG. 5 is an illustration showing the display of a pull-down menu.
Figure 6:
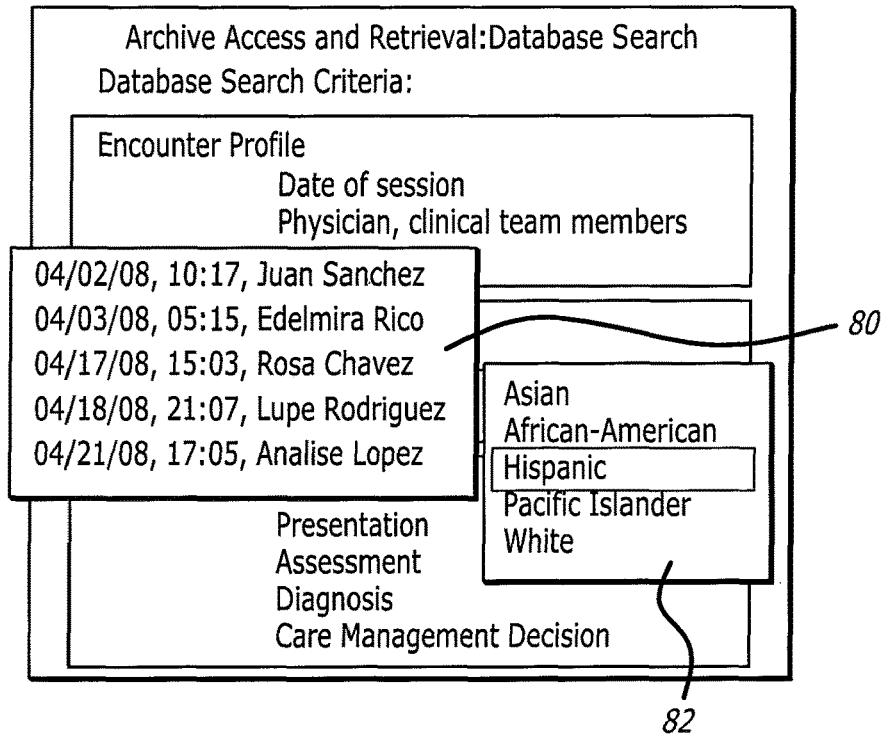
FIG. 6 is an illustration showing a session field displayed in response to the selection of a field.

The session data can be organized into a plurality of data types. FIG. 4 shows a plurality of different data types. For example, the session data can be organized into ENCOUNTER PROFILE data 70, PATIENT PROFILE data 72 and CLINICAL MANAGEMENT PROFILE data 74, with each having subfields such as EVENT and HISTORY. FIG. 5 shows a pull-down screen 78 that is displayed when a DEMOGRAPHICS field 76 is selected. FIG. 6 shows a field 80 that displays a number of sessions that match a selected HISPANIC field 82. The session data can be searched with Boolean operators such as AND and OR to search for multiple terms, data types, etc. The user can display all hits for the search, or have a statistical analysis performed based on the matching sessions.

In a factory equipment-repair application, the equipment being repaired during the session would replace the patient name in FIG. 2; and steps for repair would replace the event list in FIG. 3. Repair methodologies and affected part numbers would replace the search criteria in FIGS. 4, 5 and 6. Captured video and audio would show the steps in the repair process, and would be timestamped and cross-referenced to the data in FIG. 3.

Referring to FIG. 1, the system 10 may also include an image server 84 and a registry server 86. The image server 84 may include medical images. For example, the medical images may include CT scans of a patient's brain. The images can be downloaded to one of the remote stations 16 through the network 18. The registry server 86 may store historical data on patients. The historical data can be downloaded to a remote computer 16 through the network 18.

Figure 7:
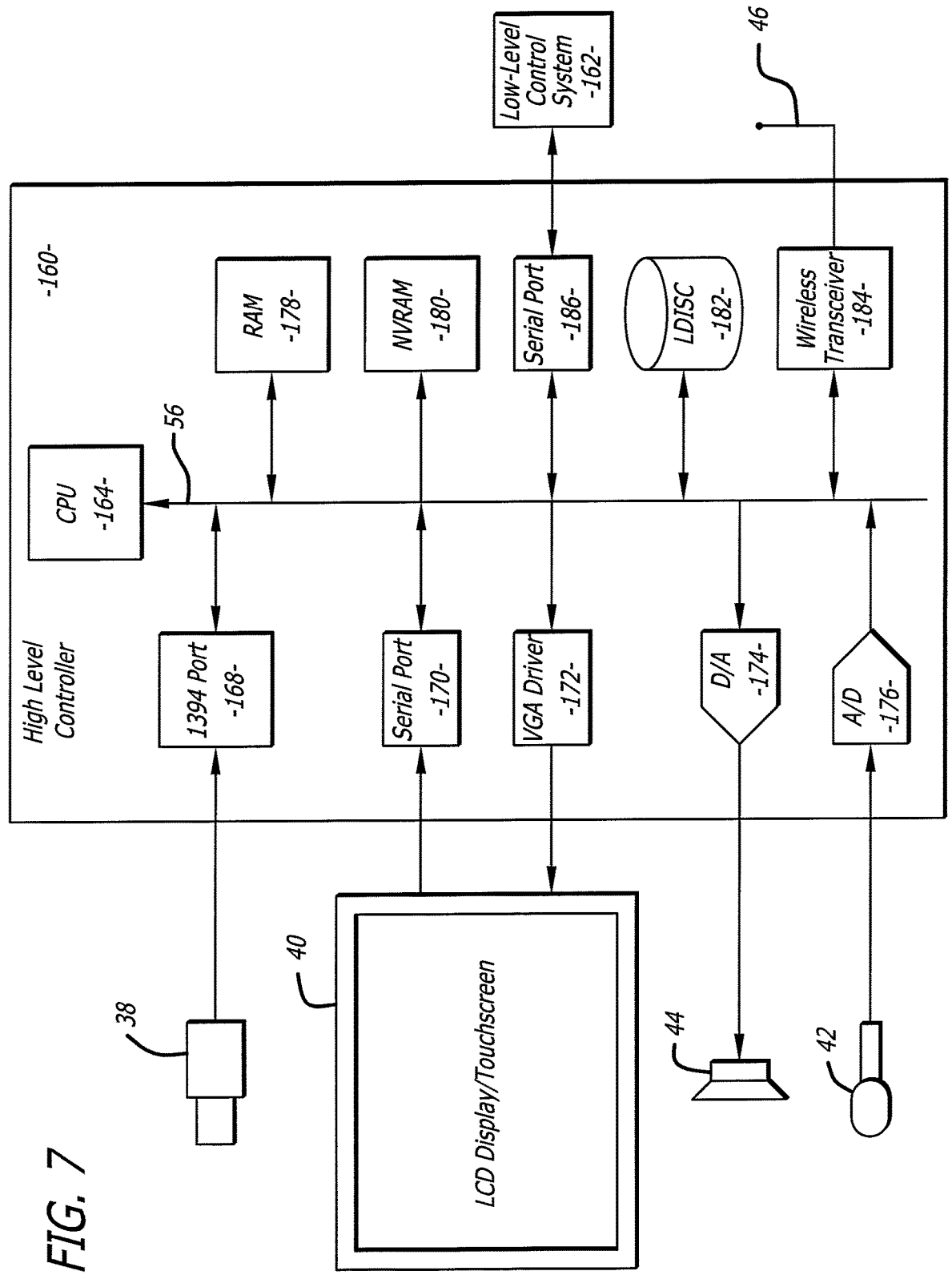
FIG. 7 is a schematic of an electrical system of a robot.

FIG. 7 shows an embodiment of a robot 12. Each robot 12 may include a high level control system 160 and low level control system 162. The high level control system 160 may include a processor 164 that is connected to a bus 166. The bus is coupled to the camera 38 by an input/output (I/O) port 168, and to the monitor 40 by a serial output port 170 and a VGA driver 172. The monitor 40 may include a touchscreen function that allows a user to enter input by touching the monitor screen.

The speaker 44 is coupled to the bus 166 by a digital to analog converter 174. The microphone 42 is coupled to the bus 166 by an analog to digital converter 176. The high level controller 160 may also contain random access memory (RAM) device 178, a non-volatile RAM device 180 and a mass storage device 182 that are all coupled to the bus 172. The RAM 178, NVRAM 180 and/or mass storage device 182 may contain session data that is transmitted to the remote station and/or server. The robot antennae 46 may be coupled to a wireless transceiver 184. By way of example, the transceiver 184 may transmit and receive information in accordance with IEEE 802.11b.

The controller 164 may operate with a LINUX OS operating system. The controller 164 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 160 operates to control communication between the robot 12 and the remote control station 16.

The high level controller 160 may be linked to the low level control system 162 by a serial port 186. The low level control system 162 may include components and software that mechanically actuate the robot 12. For example, the low level control system 162 provides instructions to actuate the movement platform to move the robot 12. The low level control system 162 may receive movement instructions from the high level controller 160. The movement instructions may be received as movement commands from the remote control station or another robot. Although two controllers are shown, it is to be understood that each robot 12 may have one controller, or more than two controllers, controlling the high and low level functions.

The system may be the same or similar to a robotic system provided by the assignee InTouch Technology, Inc. of Santa Barbara, California under the name RP-7, which is hereby incorporated by reference. The system may also be the same or similar to the system disclosed in U.S. Pat. No. 7,292,912, which is hereby incorporated by reference.

Figure 8:
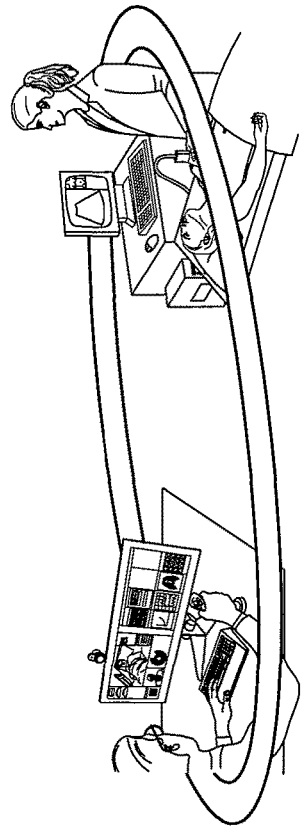
FIG. 8 is a graphical user interface of a user interface.

FIG. 8 shows a graphical user interface 250 can be provided at the user interface 58. The graphical user interface 250 includes a plurality of data fields 252 that can be filled by the user. The data fields 252 can request patient information such as name, age, etc. The data fields may also include request for medical data such as heart rate, glucose level and blood pressure ("SBP" and "DBP"). The data entered into the fields 252 can be included in the session data that is transmitted and stored by the system 10. Filling the data fields may be designated an "event" that is given as associated time stamp and displayed by a user interface.

Figure 9:
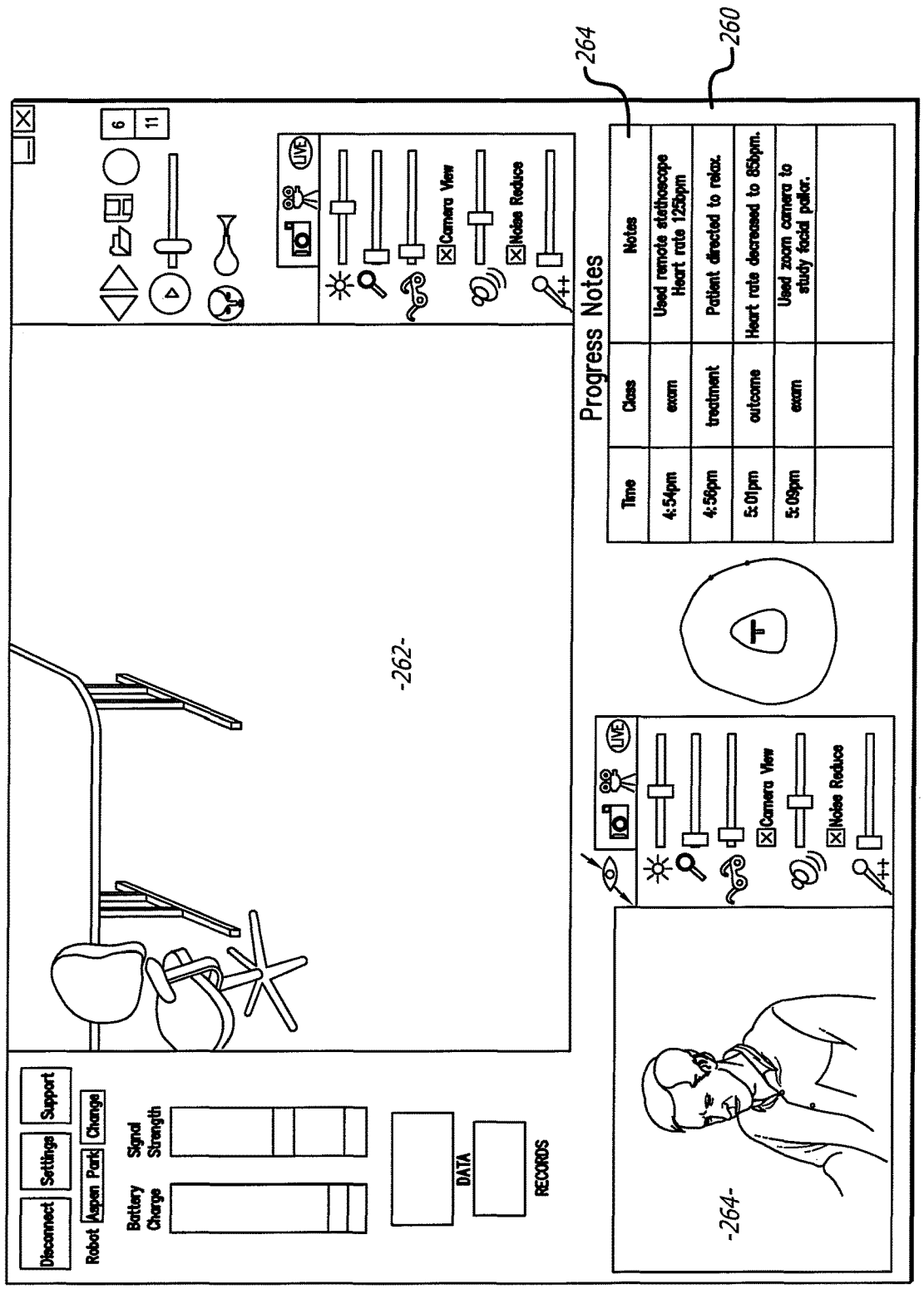
FIG. 9 is a graphical user interface at a remote station.

FIG. 9 shows a display user interface ("DUI") 260 that can be displayed at the remote station 16. The DUI 260 may include a robot view field 262 that displays a video image captured by the camera of the robot. The DUI 260 may also include a station view field 264 that displays a video image provided by the camera of the remote station 16. The DUI 260 may be part of an application program stored and operated by the computer 22 of the remote station 16. The video and any accompanying audio displayed by the robot and station view fields may be transmitted and stored by the system 10 as session data.

The DUI 260 may contain a "progress notes" text editing field, which enables a "document as you treat" methodology. As the physician conducts treatment, he can document both the treatment steps and outcomes in the progress notes field. Each note may be manually timestamped by the physician, or automatically timestamped by the software based on when the physician began typing each note. In the application of factory floor equipment repair, the progress notes would detail the various examinations and repair steps taken.

FIG. 10 shows a graphical user interface 270 that can be displayed by the monitor of the remote station 16. The interface 270 includes a "PATIENT INFO" tab 272, a "NIHSS" tab 274 and a "t-PA" tab 276. Selection of the PATIENT INFO tab 272 displays various data fields 278 including patient name, age, weight, heart rate, etc. This may be the same information entered through the user interface 250. This information may be included in the session data that is transmitted and stored by the system 10. The usage of this interface may be tagged as an event with an associated time stamp.

FIG. 11 shows an interface 280 when the "NIHSS" tab 274 is selected. The interface 280 has a data field 282 that provides a questionnaire to rate the severity of a stroke victim using the NIHSS stroke scale. This provides a readily available medical tool for the physician. The results of the questionnaire can be included in the session data and be tagged as an event that has an associated time stamp.

Figure 13:
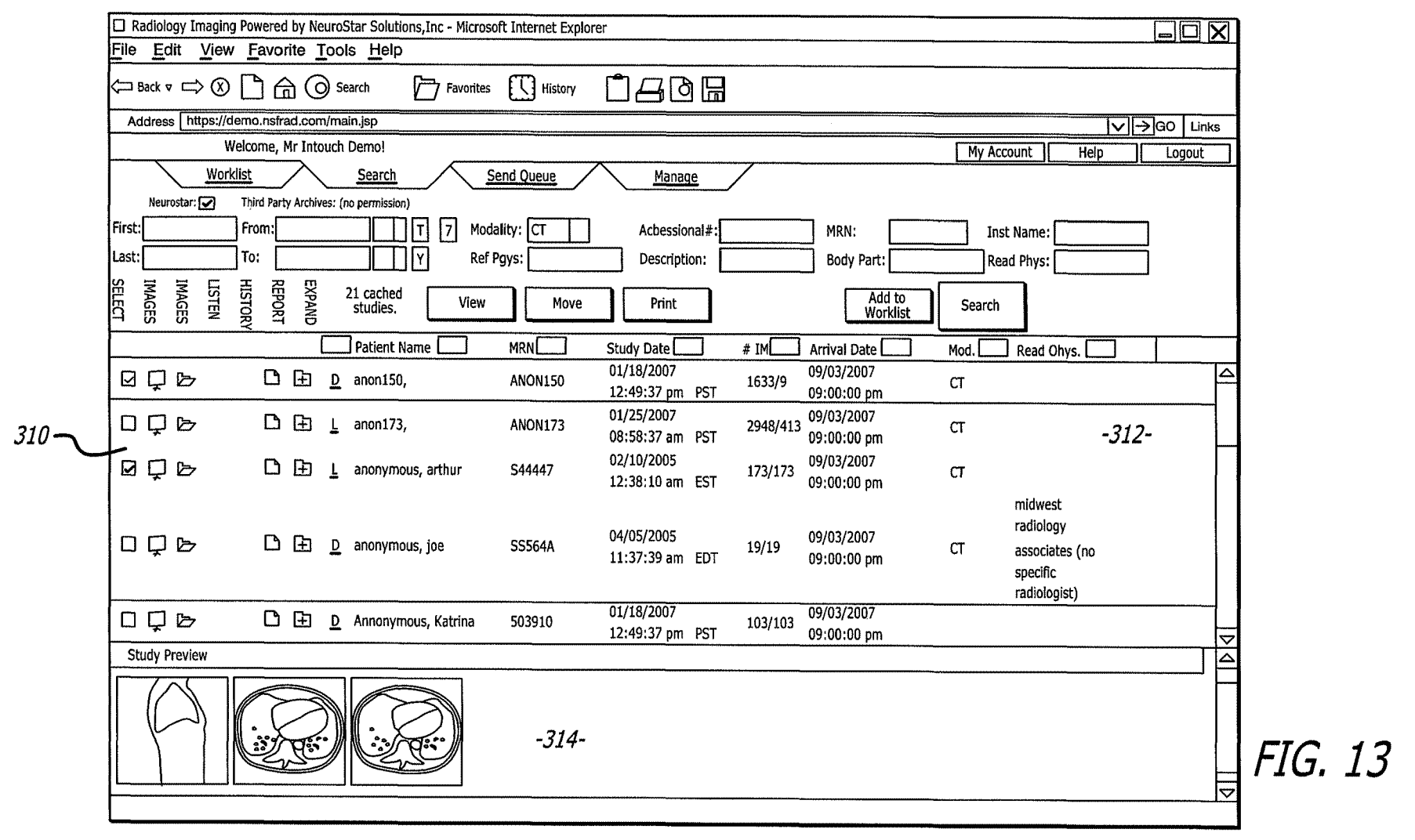

FIG. 12 shows an interface 290 when the "t-PA" tab 276 is selected. The interface 290 may include a data field 292 that provides the patient's weight, a "TOTAL DOSE" data field 294, a "BOLUS DOSE" data field 296 and an "INFUSION DOSE" data field 298. The interface 290 may also include a "CALCULATE" button 300. When the CALCULATE button 300 is selected the data fields 294, 296 and 298 are automatically populated with a calculated dosage. This provides a patient management plan for the physician to review. The interfaces 270, 280 and 290 also have a "VIEW IMAGES" button 302 that when selected displays an interface 310 shown in FIG. 13. The interface 310 includes a data field 312 and an image field 314. The image field 314 can provide a plurality of medical images such as a CT scan of the patient's head.

The calculated dosage and images can be included in the session data that is transmitted and stored by the system. The automatic population of the data fields may be tagged as an event with an associated time stamp. Likewise, the selection of the data and/or image fields may be tagged as events with time stamps.

The system is useful for allowing a physician to remotely view and treat a stroke patient. The system provides patient information, NIHSS stroke severity assessment, calculated t-PA dosage and CT head images that allow the physician to provide real time remote patient treatment. The system also allows such sessions to be audited so that medical personnel, healthcare institutions, insurance carriers, etc. can audit sessions. Such audits may include viewing video/audio captured by the robot during a session.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical telepresence system, comprising:
a telepresence device in the vicinity of a patient, said telepresence device has a patient camera, a patient monitor, a patient microphone, and a patient speaker;
a remote station that has a station camera, a station monitor, a station microphone, and a station speaker, said remote station and said telepresence device are configured to establish a telepresence session during which:
said station monitor is coupled to said patient camera and configured to display a patient video captured by said patient camera,
said patient monitor is coupled said station camera and configured to display a station video captured by said station camera,
said station speaker is coupled to said patient microphone and said patient speaker is coupled to said station microphone to enable two-way audio communication between said telepresence device and said remote station, and
said remote station is configured to control said telepresence device,
wherein said telepresence session results in session content data that includes at least a portion of both the audio captured by the patient microphone and the video captured by the patient camera and at least one of a physician note, a diagnosis, and a prescription information; and,
a records server configured to store said session content data in association with a unique identifier and provide said stored session content data to a terminal via a network after said telepresence session is concluded, wherein said terminal is configured to reproduce said session content data, including the session audio and video.

2. The system of claim 1, wherein said session content data is entered by an operator at the remote station.

3. The system of claim 1, wherein said session content data is correlated with a movement of said telepresence device.

4. The system of claim 1, wherein said session content data is searchable.

5. The system of claim 1, wherein said session content data includes at least one time stamp.

6. The system of claim 5, wherein said remote station provides a graphical user interface that displays said time stamp and said session content data.

7. The system of claim 6, wherein said session content data is entered by an operator at said remote station.

8. The system of claim 7, wherein said time stamp is automatically generated when said session content data is entered by the operator.

9. The system of claim 1, further comprising a billing server that generates a bill with said session content data.

10. The system of claim 1, further comprising a bill that is based on an action of said session content data.

11. The system of claim 1, wherein said session content data is structured into a plurality of data types and is searchable across said data types.

12. A method for conducting a medical tele-presence session, comprising:
controlling a telepresence device in the vicinity of a patient through control of a remote station, the telepresence device has a patient camera, a patient monitor, a patient speaker, and a patient microphone, the remote station includes a station camera, a station monitor, a station speaker, and a station microphone;
establishing a telepresence session during which the station monitor is coupled to the patient camera and displays a patient video captured by the patient camera, said patient monitor is coupled to the station camera and displays station video captured by the station camera, the station speaker is coupled to the patient microphone, and the patient speaker is coupled to the station microphone to enable two-way audio communication between said telepresence device and the remote station;
generating session content data that includes session audio captured by the patient microphone, session video captured by the patient camera, and at least one of a physician note, a diagnosis, and a prescription information;
storing the session content data generated during the telepresence session in a records server in association with a unique identifier;
accessing and reproducing said session content data, including the session audio and video, stored in the server at a terminal via a network after said telepresence session is concluded.

13. The method of claim 12, wherein the session content data is searchable.

14. The method of claim 12, further comprising generating at least one time stamp for the session content data.

15. The method of claim 14, further comprising displaying the time stamp and the session content data.

16. The method of claim 15, wherein the session content data is entered by an operator at the remote station.

17. The method of claim 16, wherein the time stamp is automatically generated when the session content data is entered by the operator.

18. The method of claim 12, further comprising transmitting a video image of a user at the control station to a monitor of the robot.

19. The method of claim 12, further comprising automatically generating a bill with the session content data.

20. The method of claim 12, further comprising structuring the session content data into a plurality of data types and searching the session content data across the data types.

* * * * *